United States Patent
Müller-Lierheim et al.

(10) Patent No.: US 8,759,414 B2
(45) Date of Patent: Jun. 24, 2014

(54) POLYMER COMPOSITION HAVING A HIGH REFRACTIVE INDEX

(75) Inventors: Wolfgang Müller-Lierheim, Munich (DE); Joachim Storsberg, Worstadt (DE); André Laschewsky, Potsdam (DE); Eckhard Görnitz, Teltow (DE); Elsbeth Winter, Memmingen (DE)

(73) Assignee: Coronis GmbH, Munich (DE)

( * ) Notice: Subject to any disclaimer, the term of this patent is extended or adjusted under 35 U.S.C. 154(b) by 736 days.

(21) Appl. No.: 12/095,897

(22) PCT Filed: Dec. 1, 2006

(86) PCT No.: PCT/EP2006/011557
§ 371 (c)(1),
(2), (4) Date: Nov. 17, 2008

(87) PCT Pub. No.: WO2007/062864
PCT Pub. Date: Jun. 7, 2007

(65) Prior Publication Data
US 2009/0247661 A1    Oct. 1, 2009

(30) Foreign Application Priority Data
Dec. 1, 2005 (EP) .................... 05026265

(51) Int. Cl.
*A61F 2/16* (2006.01)
*B32B 17/10* (2006.01)
*B41J 2/16* (2006.01)
*A61K 6/083* (2006.01)
*A61L 24/00* (2006.01)

(52) U.S. Cl.
USPC .......... 522/180; 522/181; 523/105; 523/106; 523/113; 623/6.11; 623/6.56

(58) Field of Classification Search
USPC ................. 522/180, 181; 523/105, 106, 113; 623/6.11, 6.56
See application file for complete search history.

(56) References Cited

U.S. PATENT DOCUMENTS

| | | | | |
|---|---|---|---|---|
| 4,543,398 A | * | 9/1985 | Bany et al. | 525/474 |
| 5,475,074 A | * | 12/1995 | Matsuoka et al. | 526/336 |
| 5,693,095 A | * | 12/1997 | Freeman et al. | 623/6.56 |
| 6,036,891 A | | 3/2000 | Liao et al. | |
| 2004/0155312 A1 | | 8/2004 | Muller-Lierheim | |

FOREIGN PATENT DOCUMENTS

| | | |
|---|---|---|
| EP | 0485197 A1 | 5/1992 |
| EP | 0898972 A2 | 3/1999 |
| EP | 1512704 A1 | 3/2005 |
| JP | 53034853 | 3/1978 |
| JP | 05304853 | 11/1993 |

* cited by examiner

*Primary Examiner* — Michael Pepitone
*Assistant Examiner* — Jessica Roswell
(74) *Attorney, Agent, or Firm* — Seed IP Law Group PLLC

(57) ABSTRACT

Described is the use of polymers with a high refractive index for ophthalmic products and a process for the production thereof.

20 Claims, No Drawings

POLYMER COMPOSITION HAVING A HIGH REFRACTIVE INDEX

The invention concerns the use of a polymer composition with a high refractive index in opthalmology and a process for the production of the polymers.

In accordance with the invention there are provided polymer compositions with a high refractive index, which are particularly suitable for use for eye implants. In particular intraocular lenses (IOL), corneal implants, keratoprostheses and so forth are to be considered as eye implants. Intraocular lenses have already long been known. They are surgically inserted into the eye and replace the natural lens of the eye in order to restore the vision to a patient suffering from a clouded or damaged lens. The natural lens has to be replaced if it was damaged for example in an accident or, and this is generally the case, if the lens is clouded due to a cataract.

Intraocular lenses can be produced from hard or soft polymers. Hard polymers have the advantage that they are mechanically stable and good to process. They are however difficult to use. The intraocular lens is generally pushed into the eye, after a surgical incision has been made. It is therefore desirable for the lens to be flexible so that the incision can be kept as small as possible. If the polymer used for the lens is so elastic that the lens can be folded or if the material is so flexible that it can be rolled up, the incision can be made even smaller. That is advantageous and desirable so that damage to the eye is minimised and healing takes place more quickly.

Soft lenses can be inserted well, but they frequently lack stability in respect of shape. In addition intraocular lenses must have such elastic properties that on the one hand they can be folded together or rolled up, but on the other hand, after having been inserted, they resume their original shape and also retain that shape. The material for intraocular lenses may not be excessively soft and may also not have a memory effect. Polymers suitable for intraocular lenses must therefore unite a combination of mutually contradictory properties.

A further essential requirement for a polymer which is to be inserted into the eye is a sufficiently high refractive index. The action of an optical lens, with a predetermined geometry, is correspondingly greater, the more the refractive index differs from that of the surrounding medium. Accordingly, a lens can be correspondingly thinner, the higher the refractive index of the material from which it is made. Known materials generally have a refractive index in the range of between 1.45 and 1.56 so that intraocular lenses made from those materials must be relatively thick. However, the thicker the lens is, the more difficult it is to insert. Transparent polymers with a refractive index (measured in relation to volume) of more than 1.60 are therefore desirable.

A further condition for a polymer suitable for the production of eye implants is transparency. Suitable polymers must have a high degree of light transparency, in which respect certain wave ranges can possibly be filtered out by the additional of suitable ingredients.

The glass transition temperature is also a parameter to be borne in mind. It must at any event be below 37° C. so that the lenses are processable at body temperature. A glass transition temperature in the region of less than 15° C. is considered to be suitable and a temperature of less than 10° C. is considered to be desirable.

Acrylates and methacrylates have already long been used for the production of intraocular lenses and eye implants, because of their good compatibility. It will be noted however that homopolymers of the monomers which are usually employed have inadequate strength properties and their refractive index is generally too low. The attempt has therefore been made to improve those properties by copolymerisation. There are very many different approaches in that respect.

To increase refractive power, it has been proposed that phenyl-bearing acrylates and methacrylates may be used. Combinations of hydrophobic and hydrophilic components have also been employed to impart advantageous properties to the material. Thus for example EP 0 898 972 discloses a material for soft intraocular lenses, which is obtained by polymerisation of a hydrophilic monomer with an aromatic (meth)acrylate, an alkyl(meth)acrylate and a crosslinkable monomer. The hydrophilic monomer can be for example (meth)acrylamide and the aromatic (meth)acrylate can be for example phenyloxyethyl acrylate. Flexibility of the material is to be improved by the alkyl(meth)acrylate.

Aryl-bearing acrylates are also proposed in EP 0 667 966, wherein an aryl-bearing component is combined with one or two further components without aryl groups. EP 0 774 983 also describes copolymers which are made up of an aryl group-bearing acryl monomer and a second hydrophilic, in particular hydroxy group-bearing acrylate or methacrylate. To produce polymers with a high refractive index, EP 0 485 197 proposes copolymerising at least two monomers, namely an aryl acrylate and an acryl methacrylate. A third monomer serves to crosslink the polymer.

EP 1 077 952 discloses a polymer composition in which a special benzotriazine monomer is used in combination with acrylamides to improve the properties.

What is common to all polymers mentioned in the state of the art is that they are made up of at least three monomers to achieve an optimum combination of refractive index and mechanical properties.

None of the previously known materials is satisfactory in regard to a combination of good mechanical properties and high refractive index.

Therefore an object of the present invention was to provide a polymer composition which unites excellent mechanical properties with a high refractive index, preferably over 1.56. A further object was to provide a polymer material which on the one hand is so elastic that it can be folded and rolled and on the other hand is of such a strength that it is mechanically stable in the eye. A further object of the invention was to provide a material which is biologically compatible and which can be easily manufactured.

According to the invention a polymer composition is used which is made up of at least one main monomer a) of the formula:

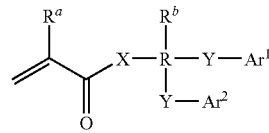

wherein X can be O or $NR^c$,
Y can be O, S or $NR^c$ respectively,
R is a straight, branched or cyclic hydrocarbon residue with 1 to 6 carbon atoms,
$R^a$ is hydrogen or a methyl residue,
$R^b$ can be hydrogen, $C_1$-$C_5$ alkyl residue or Y—$Ar^3$,
$R^c$ is hydrogen, a straight, branched or cyclic hydrocarbon residue with 1 to 6 carbon atoms or an aryl group,
$Ar^1$, $Ar^2$ and $Ar^3$ are respectively independently of each other an aryl group which is bonded to Y by way of a bond or by way of ($-CH_2$)$_n$, wherein n can be 0, 1, 2 or 3, and wherein the aryl group can be substituted with 1 to 4 substituents, selected from $C_1$-$C_5$ alkyl, $C_1$-$C_5$-alkoxy, mono- and disubstituted amino, wherein the substituents can be selected from residues $R^c$ as defined hereinbefore, b) a crosslinking monomer, and c) optionally further monomers for adjusting properties such as refractive index, surface properties, glass transition temperature, strength properties, UV absorption or for colouring, wherein the main monomer a) is contained in an amount of at least 20% by weight, preferably at least 40% by weight, particularly preferably at least 60% by weight.

Preferably the compounds used as monomer a) are those in which Ar respectively denotes a phenyl residue which has 0, 1 or 2 substituents, selected from alkyl and alkoxy residues.

The following compounds are particularly preferably used as monomers:

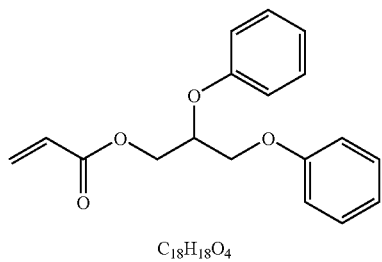

$C_{18}H_{18}O_4$

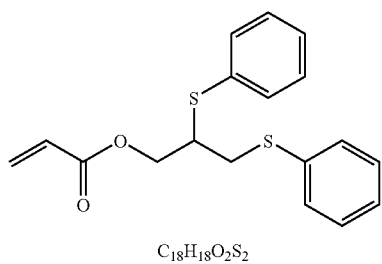

$C_{18}H_{18}O_2S_2$

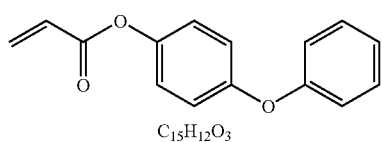

$C_{15}H_{12}O_3$

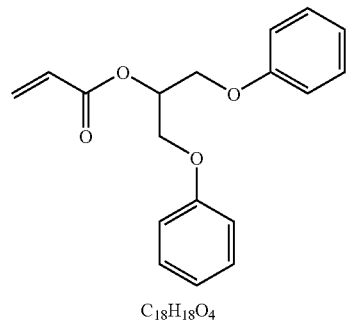

$C_{18}H_{18}O_4$

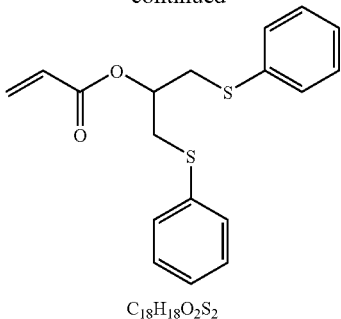

$C_{18}H_{18}O_2S_2$

It was surprisingly found that the material according to the invention is particularly well suited to use in the eye as it combines useful properties which were hitherto not available in that combination. The material according to the invention has a very high refractive index which allows it to manufacture eye implants of very thin cross-section which satisfy the optical demands. Furthermore the polymers according to the invention can be used for the manufacture of intraocular lenses which have superior mechanical properties so that the intraocular lenses can be inserted in a very careful fashion. The polymers are also suitable for other ophthalmic devices such as contact lenses, keratoprostheses, corneal rings or inlays. The respectively optimum properties can be well set by a combination of the monomers.

The polymer material according to the invention is made up from the above-mentioned monomers a), b) and optionally c). A crosslinking monomer—monomer b)—must always be used to achieve adequate stability in respect of shape. The polymer is substantially made up from the component a) as the main monomer, wherein at least 20% by weight, preferably at least 40% by weight and particularly preferably at least 60% by weight of the monomers is formed by the monomer a). In general smaller proportions of further monomers which contribute special properties form the balance.

In a preferred embodiment which is referred to as a 'homopolymer' the polymer material substantially comprises monomer a), wherein, as mentioned above, monomer b) is also used for crosslinking purposes.

The term homopolymer is used here to denote a polymer material in which monomer a) forms the substantial proportion, that is to say more than 85%, particularly preferably more than 90% of the monomers.

In a further preferred embodiment the polymer is formed from monomer component a), crosslinker b) and optionally further monomers c) as well as a further proportion of a monomer d) which is copolymerised to achieve particular properties. The additional monomer d) used for copolymerisation replaces a part of monomer a) and must be compatible with the compounds used as monomers a) and b). In an embodiment the additionally added monomer d) is a monomer with a structure as shown in formula I but which is substituted on the aryl residues, at least in part, with halogens, in particular fluorine, iodine or bromine atoms.

The balance of the material is formed by crosslinkers and optionally one or more additional components selected from the group consisting of UV light-absorbent compounds, blue light-absorbent compounds, dyestuffs, components which alter given properties, and so forth.

It is however also possible to copolymerise other monomers which are usually employed in materials for eye implants, examples in that respect are to be found in the specified literature documents.

The present invention therefore uses a polymer material which is suitable as a foldable IOL material and which in an embodiment can be so polymerised that substantially only two monomers—monomer a) and crosslinker b)—are used. That reduces or eliminates difficulties such as physical/chemical heterogeneity.

The polymer composition according to the invention, in an embodiment, can thus be a homopolymer which is substantially made up only of monomer a) and crosslinked with monomer b). However—besides the crosslinking monomer—the polymer composition according to the invention can also be made up from further monomers. In any case, a crosslinking monomer is necessary, which is copolymerised with the monomer a) and optionally the further monomers.

In accordance with the invention, the term copolymers is also used to denote materials which were polymerised from two different monomers according to the invention and at least one crosslinker or at least one monomer according to the invention, a crosslinker and at least one further monomer.

The polymers used according to the invention can be both statistical polymers and also block copolymers, wherein blocks of monomers according to the invention and blocks of other monomers can afford advantageous properties.

Those compounds which have at least two bondable functional groups are used as crosslinking monomers. Examples of suitable functional groups are vinyl, acrylate, methacrylate, hydroxy and thiol groups. Suitable crosslinking compounds are divinylbenzene, dithioresorcin, bisphenol A-methacrylate. In accordance with the invention, as crosslinking monomers it is possible to use the per se known compounds, inter alia any compound terminally ethylenically unsaturated with more than one unsaturated group. Suitable crosslinking agents are known to the man skilled in the art in this field and the monomers usually employed can also be used for the polymers according to the invention. Examples of known crosslinkers are for example the following bifunctional compounds: ethylene glycol dimethacrylate; diethylene glycol dimethacrylate; allyl methacrylate, propane-1,3-diol dimethacrylate; propane-2,3-diol dimethacrylate; hexane-1,6-diol dimethacrylate; butane-1,4-diol dimethacrylate; $CH_2=C(CH_3)C(=O)O-(CH_2CH_2O)_n-C(=O)C(CH_3)=CH_2$, wherein n=1 to 50 and $CH_2=C(CH_3)C(=O)O-(CH_2)_tO-C(=O)C(CH_3)=CH_2$, wherein t=3 to 20, and the corresponding acrylates. Desirably the degree of polymerisation of the crosslinking compound is so selected that the number-average molecular weight is about 400, about 600 or, most preferably, about 1000.

Particularly good properties are achieved however if a compound of the following formula II is used as the crosslinker:

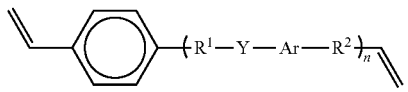

which at each of the two ends bears a respective terminally unsaturated group, wherein Y can denote O or S, Ar is an aromatic, in particular phenyl residue which can be substituted with 0 or 1 to 4 substituents which are selected from $C_1$-$C_5$ alkyl residues, $C_1$-$C_5$ alkoxy residues and halogens, wherein n can be an integer of 1 to 4 and preferably 1 or 2, wherein $R^1$ and $R^2$ is a bond or a $(CH_2)_m$ residue wherein m is 1, 2 or 3.

Particularly preferably the following compounds are used as the crosslinker:

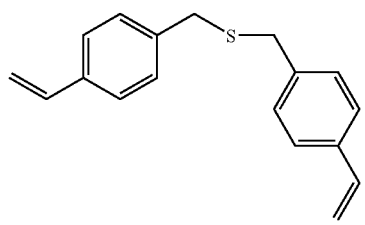

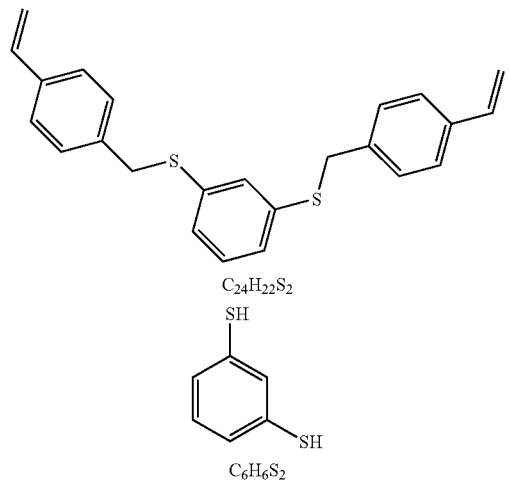

It was found that, when using the monomers a) according to the invention, polymers with a refractive index of far above 1.55 are produced. The refractive index can be up to 1.6 and above. In a particularly preferred embodiment monomers are used in which Y denotes sulphur. Those monomers produce polymers with a refractive index of over 1.6.

In general only one kind of crosslinking monomer is used for the polymer according to the invention. It is however also possible to use a combination of various crosslinkers. For example, it is possible to use a mixture of various monomers of the formula II or a mixture of monomers of the formula II with one or more usual crosslinkers.

In general terms the total amount of the crosslinking component is at least 0.1% by weight and in dependence on the nature and concentration of the remaining components and the desired physical properties, it can be in a range of up to 20% by weight. The preferred range of concentration for the crosslinking component is 0.1 to 15% by weight. If the amount of crosslinker is excessively low the elastic properties of the polymer can be adversely affected. If on the other hand the proportion of the crosslinking component exceeds 20% by weight the polymer can be too brittle for the intended purpose of use.

Hydrophobic polymers made up from acrylates and methacrylates can be sticky. That stickiness is disadvantageous in terms of use as an eye implant, in particular as an IOL, as, when the implant is rolled up or folded, the surfaces stick to each other and thus are not easy to separate. To influence the surface properties of the polymer composition according to the invention, it is possible to add a further monomer d) which is similar to the monomer a) but which carries at least one fluorine atom or a perfluoro group as a substituent. The fluorine substituent can be bonded to the aryl residue or possibly to the alkyl component. In a preferred embodiment the fluorinated monomer used is such a monomer which is structurally identical to the main monomer but which as a substituent has halogen or fluorine atoms. Such a combination is advantageous as the monomers are compatible with each other and lead to homogeneous materials. If halogenated monomers are used the proportion thereof should not be above 10% by weight with respect to the amount of all monomers. A range of 3 to 8% is preferred.

If the problem of stickiness occurs, in a preferred embodiment either a proportion of the main monomer a) or a proportion of the copolymerising monomer d) or a proportion of the monomers a) and the monomers d) can be copolymerised in fluorinated form.

It may further be useful to employ a proportion of a monomer in accordance with formula I in iodinated or brominated form. Iodinated and brominated compounds increase the refractive index of the material polymerised therefrom and are therefore advantageous.

The proportion of the halogenated monomers, preferably fluorinated monomers, if present, is in a range of 0.05 to 10% by weight with respect to the weight of the overall polymer composition. Preferably halogenated monomers are included in a proportion of 0.1 to 3%. If the proportion of the halogenated monomer is excessively high the refractive index is excessively influenced. On the other hand, with an excessively low amount, the influence on the surface properties is too low to be perceptible. Depending on the main monomers used, the nature and amount of the halogenated monomer can be adjusted by the man skilled in the art in a few routine experiments.

As further ingredients for the polymer material according to the invention it is possible to mention ingredients which are known for that kind of polymer system such as initiators, dyestuffs and so forth. In general all additives are polymerised into the polymers and are not added separately so that compounds cannot be leached out.

Polymerisation is usually started by an initiator which is added to the material to be polymerised. Both compounds which are activatable by heat and also compounds which are activatable by light can be used for the composition according to the invention. As polymers used in the region of the eye generally include UV absorbers, it is undesirable to use UV initiators. Therefore either blue light initiators which are known per se to the man skilled in the art or compounds activatable with IR beams or heat are preferably used.

Preferred thermal initiators are for example compounds with peroxy residues such as t-butyl(peroxy-2-ethyl)hexanoate and di(tert.-butylcyclohexyl)peroxydicarbonate which are frequently used for the polymerisation of intraocular lenses. Suitable photoinitiators are those which are usually employed such as azo compounds, for example MAIB, phosphine oxide compounds such as benzoyl phosphine oxide, in particular 2,4,6-trimethylbenzoyldiphenyl phosphine oxide. Initiators are added in per se known amounts, for example in a typical embodiment in an amount of 5% by weight or less.

UV absorbers are frequently added for polymers which are used in the eye to protect the eye from damage due to UV radiation. Benzene triazol compounds are frequently selected for that purpose. A known reactive UV absorber is for example 2-(2'-hydroxy-3'-methallyl-5'-methylphenyl)benzene triazol. UV absorbers are typically present in an amount of 0.1 to 5% by weight.

The nature and amount of the above-mentioned, optionally additional components are determined by the desired properties of the finished ophthalmic implant. Preferably ingredients and the proportions thereof are so selected that the polymers of the present invention have the desired optical and mechanical properties which make the materials of the present invention particularly suitable for use in the eye.

The lens material preferably has a refractive index in the dry state of at least 1.60. If a higher proportion of sulphur-bearing monomers is polymerised to give the material according to the invention it is also possible to attain values of more than 1.60, which is particularly preferred.

For a given optical diameter, optics which are made from materials with a refractive index of below 1.50 are necessarily thicker than optics of the same refractive power which are made from materials with a higher refractive index. The thinner the optic member can be, the correspondingly smaller will the incision be, by way of which the implant is introduced into the eye.

The polymer used according to the invention has advantageous mechanical properties by use of the monomers a) and b). In particular the polymer is such that an eye implant made therefrom generally does not break, tear or split when it is folded or rolled.

According to the invention the above-described polymer composition is used in the area of opthalmology. Surprisingly, the above-described polymers unite the properties necessary for ophthalmic applications such as low or no toxicity, suitable mechanical properties such as suitable flexibility and a high refractive index. The polymer composition can therefore be used in many cases in the ophthalmic field for any kind of ophthalmic device. Use as an implant, in particular a corneal implant or an IOL, and in the form of contact lenses, keratoprostheses, corneal rings and corneal inlays etc is particularly suitable.

Intraocular lenses which are constructed from the materials of the present invention can be made up in per se known manner, the structure depending on whether they are rolled or folded to give a small cross-section which can fit through a relatively small incision. The intraocular lenses can for example be of a one-piece or multi-piece structure and have optical and haptic components. The optical part is the part which serves as the lens. The haptics are fixed to the optical portion and hold the optical portion in its correct position in the eye. The optical portion and the haptic or haptics can be formed from the same polymer or can comprise different materials. In the case of an IOL which is referred to as multi-piece, the optical portion and the haptic or haptics are made separately and then the haptics are fixed to the optical portion. In the case of a one-piece lens the optical portion and the haptics are formed from polymer. Shaping and processing of the optical portion and the haptic is effected in a manner which is well known to the man skilled in the art.

Both hydrophobic and also hydrophilic polymer compositions can be produced with the monomers according to the invention. If a hydrophobic polymer is wanted monomer a) can be processed as a homopolymer or with further hydrophobic comonomers. If a hydrophilic polymer material is wanted the monomer a) according to the invention is copolymerised with a hydrophilic monomer which for example can be an acrylate or methacrylate with hydroxy groups.

A further parameter which is important for the processing properties of polymers is the glass transition temperature. The glass transition temperature influences the flexibility of the material. If the glass transition temperature is very high the material is brittle at body temperature and room temperature, if the glass transition temperature is very low the material can scarcely be processed at usual temperatures. Therefore, for use as eye implants, polymers are desirable which have a $T_g$ of 15° C. or less, preferably 10° C. or less, as in that case polymers are obtained which can be well processed and which nonetheless still maintain their elastic properties at body temperature. In order to set an optimum glass transition temperature with the polymer made from the above-specified monomers, a monomer is preferably added, which sets the glass transition temperature into the desired range. Monomers suitable for that purpose are known to the man skilled in the art and the appropriate monomer and the amount thereof to be used can be established in a few routine experiments.

Eye implants according to the invention can be still further improved by adding nanopigments as are known per se to the polymers. It is known from DE 101 29 787 to incorporate optical components into materials for eye implants. Optical components used are substantially transparent fillers with a higher refractive index than that of the surrounding material and of a particle size at which substantially no light scatter occurs in the component material. The optically clear or transparent filler has a high electron density which leads to an increased refractive index. That high electron density can be achieved by oxides which are difficult to dissolve, with highly charged cations, for example by heavy metal, in particular lead and bismuth compounds. Those heavy metal compounds are in crystalline and in particular nanocrystallinely deposited form, for example as silicates, germanates, aluminates or titanates. The heavy metals are fixedly integrated in the crystal matrix and are not dissolved out in the biological medium of the eye. The fillers therefore do not adversely affect the biological compatibility of the transparent component material or implant material in which they are distributed in finely distributed particle form, in particular as nanoparticles. A filler which is preferably used is rutile. That filler is biocompatible. It is inert and difficult to dissolve, thermally stable and thus autoclavable. It is also available in relatively large amounts. That filler can be deposited in nanocrystalline form and can thus be produced technically with a particle size at which practically no light scatter is induced in the component material.

When using 20% by volume of rutile as filler in an acrylate with a refractive index of n=1.5, the refractive index of the acrylate can be increased to 1.78 by the filler. In that way it is possible to increase the effective refractive index difference between the eye implant and the surrounding aqueous humour by a factor of 2 to 3.5. That makes it possible to produce for example intraocular lenses of reduced thickness and with an improved foldability.

In a preferred embodiment therefore up to 20% by weight and preferably 5 to 15% by weight of nanoparticles, as described above, is added to the polymer which is to be processed to give an IOL.

A further subject of the invention is a process for the production of the polymer composition according to the invention. Processes for the production of acrylate and methacrylate polymers are known per se. In particular bulk polymerisation and emulsion polymerisation, preferably emulsion polymerisation, are considered for the production of eye implants.

In a preferred embodiment monomers are converted into prepolymers using an initiator I and freed as far as possible of their residual monomer content. The prepolymers are then converted to the final polymer in the presence of an initiator II, optionally with the addition of monomers which influence certain properties. The initiators I and II can be the same or different, depending on the nature of the monomers used and the desired properties of the polymer. Preferably initiator I and initiator II are the same. That kind of method leads to a very low residual monomer content, which is advantageous for the planned use.

Furthermore homogenous materials are afforded by using a two-stage process in which prepolymers are produced in a first stage and they are then further polymerised with monomeric crosslinkers. The homogeneity of the material is an important parameter for use as an eye implant. Non-homogeneous regions in a polymer lead to optical flaws, which is not acceptable for eye implants.

In accordance with the invention there are provided polymer compositions which combine good mechanical properties with a high refractive index. Those polymers can be produced in a simple fashion, using usual processes.

The polymer compositions according to the invention are particularly well suited for use as corneal transplants and intraocular lenses. Subject-matter of the invention is therefore also the use of a polymer composition, as defined hereinbefore, as a corneal implant or an IOL.

The invention is further described by the following Examples which however are in no way to be interpreted as limiting.

The products obtained were investigated with $^1$H- and $^{13}$C-NMR spectroscopy. An INNOVA 500 spectrometer (Varian Inc) was used and the measurements were carried out on that spectrometer at room temperature (21° C.) with the following measurement frequencies: $^1$H-NMR: 499.84 MHz, $^{13}$C-NMR: 125.69 MHz. $CD_2CL_2$ and $CD_3OD$ were used as solvents.

EXAMPLE 1

Synthesis of

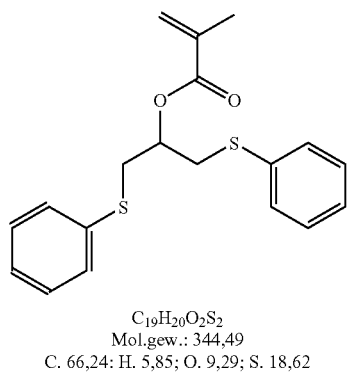 [SMILES: C=C(C)C(=O)OC(CSc1ccccc1)CSc1ccccc1]

$C_{19}H_{20}O_2S_2$
Mol.gew.: 344,49
C. 66,24: H. 5,85; O. 9,29; S. 18,62

(In the Above Mol.Gew. Means Molecular Weight)

Reaction Equation

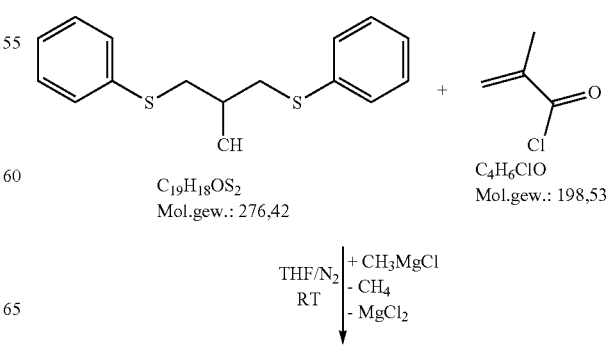

-continued

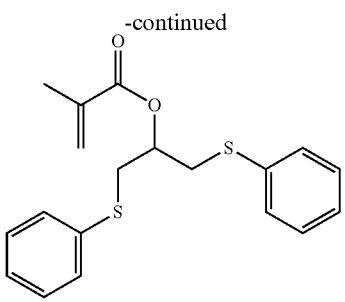

C$_{19}$H$_{20}$O$_2$S$_2$
Mol. gew.: 344.49
C. 66.24:H. 5.85:O. 9.39:S. 18.52

(In the Above Mol.Gew. Means Molecular Weight)
Reagents:
Methacryloyl Chloride

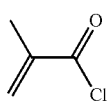

Methylmagnesium Chloride

Experimental Part

2-Methacrylic acid-2-phenylsulphanyl-1-phenylsulphanylmethyl-ethylester 1,3-Bisphenylsulphanyl-propan-2-ol was reacted with methylmagnesium chloride and methacrylic acid chloride in equimolar proportions (proportion 0.03618 mol respectively).

1,3-Bisphenylsulphanyl-propan-2-ol (MW=276.42): (10 g=0.03618 mol) was dissolved in THF which had been previously distilled over Na/K. Added to that solution was 0.03618 mol of methylmagnesium chloride [Acros, 22% by weight solution in THF] (MW=74.79)=(2.71 g (corresponds to 12.32 g of a 22% by weight solution)). That solution was then slowly added to the following solution through a dropping funnel: 0.03618 mol of methacryloyl chloride [97.0% (GC)] (MW=104.53)=(3.78 g (that is to say 3.89 g of the 97.0% preparation)) in about 100 ml of THF. The reaction solution did not heat up noticeably, cooling was not required; the solution remained clear, slightly yellowish. Stirring was effected at room temperature in a nitrogen atmosphere. The reaction was monitored by way of DC. The mixture was then heated for about 2 hours at 45 to 50° C. Stirring was effected overnight at room temperature in an N$_2$ atmosphere. Filtration of the reaction solution was effected over a G3 frit which was coated with aluminium oxide [Acros, aluminium oxide, activated, basic] and sea sand and which was previously formed into a paste with THF. The THF was then removed on the rotational evaporator and the product then further cleaned with column chromatography.

EXAMPLE 2

Synthesis of

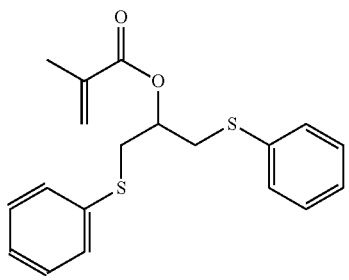

C$_{19}$H$_{20}$O$_2$S$_2$
Mol.gew.: 344,49

(In the Above Mol.Gew. Means Molecular Weight)
Reaction Equation

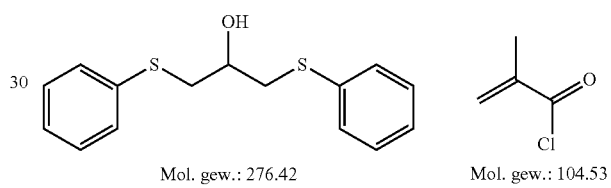

Mol. gew.: 276.42       Mol. gew.: 104.53

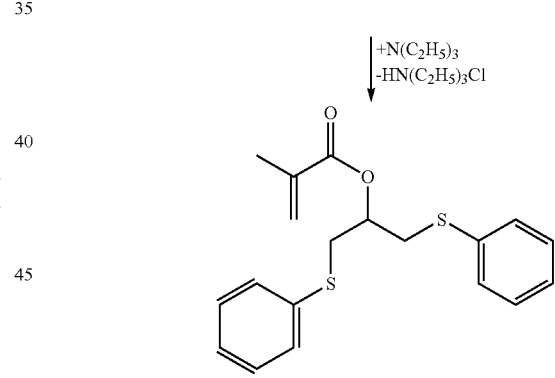

C$_{19}$H$_{20}$O$_2$S$_2$
Mol. gew.: 344.49
C. 66.24:H. 5.85:O. 9.29:S. 18.62

(In the Above Mol.Gew. Means Molecular Weight)
Chemicals
Methacryloyl Chloride (as Defined Hereinbefore)

Experimental Part 1,3-Bisphenylsulphanyl-propan-2-ol was reacted with methacryloyl chloride. The following reagents were put into a previously heated 250 ml three-necked balloon flask with condenser and N$_2$ introduction: 0.03 mol of methacryloyl chloride (3.88 g, 97%), about 60 ml of inhibitor-free, previously distilled THF as a solvent. 8.29 g of 1,3-bisphenylsulphanyl-propan-2-ol (0.030 mol) and 2.94 g of triethylamine (0.030 mol) (99% by weight) were added to a dropping funnel. The solution from the dropping funnel was allowed to drop slowly into the three-necked flask. As the reaction was not exothermic no cooling was required. A white deposit of (NEt$_3$)HCl was formed. Stirring was continued at room temperature for 1.5 hours and the resulting deposit, about 2.8 g (NEt$_3$)HCl, was then filtered off and then the THF removed on the rotational evaporator. That gave a yellow viscous liquid. The raw yield was 14 g. To clean the product obtained the liquid obtained (14 g) was dissolved in about 50 ml of CH$_2$Cl$_2$ and then shaken out with 5% NaHCO$_3$-solution. An emulsion was formed, which was broken by the addition of NaCl. Drying was then effected over Na$_2$SO$_4$ and then concentration was effected on the rotational evaporator and then with a hybrid oil pump. The result obtained was a yellow viscous liquid in a yield of about 9 g, which corresponded to 0.0267 mol or 89% of the theory. The product was then also chromatographically cleaned.

$^1$H-NMR for C$_{19}$H$_{20}$O$_2$S$_2$ (molecular weight 344.49) in CD$_2$Cl$_2$ $^1$H-NMR: 499.84 MHz in CD$_2$Cl$_2$ 7.36-7.34 ppm (4H, m, H3), 7.27-7.24 ppm (4H, m, H2), 7.19-7.17 ppm (2H, m, H1), 5.90 ppm (1H, m, H9), 5.48 ppm (1H, m, H9'), 5.12 ppm (1H, m, H6), 3.29 ppm (4H, m, H5), 1.80 ppm (3H, m, H8).

$^{13}$C-NMR: 125.69 MHz in CD$_2$Cl$_2$ 166.66 ppm (C7), 136.22 ppm (C4), 135.73 ppm (C8), 129.89 ppm (C3), 129.28 ppm (C2), 126.70 ppm (C1), 126.09 ppm (C9), 72.17 ppm (C6), 36.53 ppm (C5), 18.16 ppm (C10).

EXAMPLE 3

Synthesis of

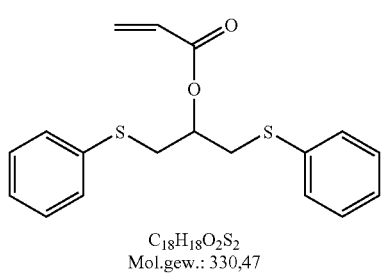 [SMILES: C=CC(=O)OC(CSc1ccccc1)CSc1ccccc1]

C$_{18}$H$_{18}$O$_2$S$_2$
Mol.gew.: 330,47

(In the Above Mol.Gew. Means Molecular Weight)
Reaction Equation

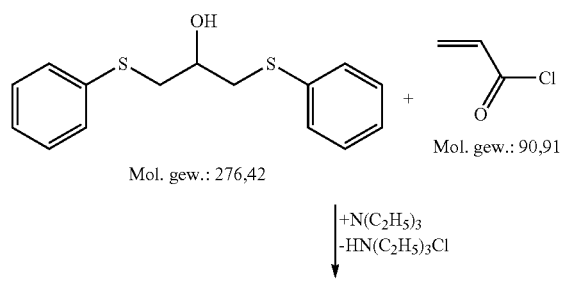

-continued

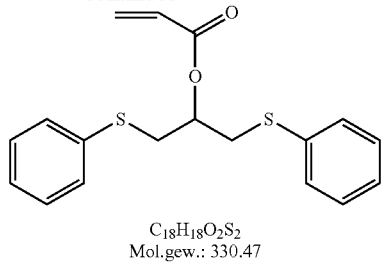

C$_{18}$H$_{18}$O$_2$S$_2$
Mol.gew.: 330.47

(In the Above Mol.Gew. Means Molecular Weight)
Reagents
Acryloyl Chloride

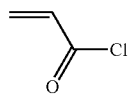

Experimental Part

Using a previously heated three-necked flask with condenser and N$_2$ introduction, 0.03 mol of acryloyl chloride as defined hereinbefore (2.828 g, 96% by weight) and 50 to 100 ml of inhibitor-free THF (previously distilled) as solvent were put into the flask. 8.29 g of 1,3-bisphenylsulphanylpropan-2-ol=0.030 mol and 0.030 mol of triethylamine [99%] (4.1 ml) were put into a dropping funnel. The solution was allowed to drop slowly out of the dropping funnel. As the reaction is not exothermic no cooling is necessary. A white deposit of (NEt$_3$) HCl was formed. Stirring was effected for a further 1.5 hours at room temperature and then the deposit was filtered off and the THF removed on the rotational evaporator. The result obtained was a yellow viscous liquid in a yield of about 9.5 g. For cleaning purposes the product was dissolved in 50 ml of inhibitor-free THF and filtered over an Alox frit to remove possible inhibitor residues. The THF was removed on the rotational evaporator and residual THF then removed with a hybrid pump (1.5 to 1.5 mbars). The result obtained was a yellow viscous liquid in a yield of about 6.8 g, which corresponds to 0.02067 mol or 68.9% of theory.

$^1$H NMR for C$_{19}$H$_{20}$O$_2$S$_2$ (molecular weight 344.49) in CD$_2$Cl$_2$ 7.33-7.37 ppm (4H, m, H3), 7.24-7.29 ppm (4H, m, H2), 7.16-7.21 ppm (2H, m, H1) 6.225 ppm (1H, dd, $^2$J (7',6)=17.1 Hz, $^2$J (7',7)=1.22 Hz, H7' (trans)) 5.93 ppm (1H, dd, $^2$J (6,7)=10.5 Hz, $^2$J (6,7')=17.3 Hz, H6) 5.755 ppm (1H, dd, $^2$J (7,6)=10.4 Hz, $^2$J (7,7')=1.22 Hz, H7(cis)) 5.13-5.15 ppm (1H, m, H5) 3.27 ppm (4H, m, H4).

EXAMPLE 4

Synthesis of

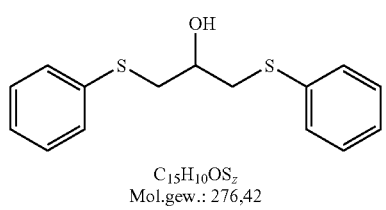 [SMILES: OC(CSc1ccccc1)CSc1ccccc1]

C$_{15}$H$_{10}$OS$_2$
Mol.gew.: 276,42

(In the Above Mol. Gew. Means Molecular Weight)

Reaction Equation

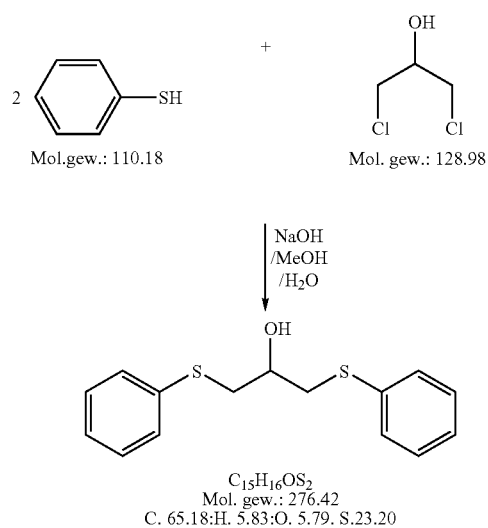

(In the Above Mol.Gew. Means Molecular Weight)
Reagents
Thiophenol [>98%]

1,3-Dichloropropan-2-ol [99%]

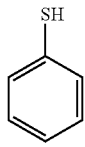

Sodium Hydroxide, Pellets with 99.998%

Experimental Part

The following were firstly added in an $N_2$ atmosphere to a 50 ml three-necked flask with condenser, dropping funnel and $N_2$ introduction: 0.05 mol of 1,3-dichloropropan-2-ol [99%] (6.449 g) dissolved in 100 ml of methanol. The following were introduced into a dropping funnel: 0.1 mol of thiophenol [98%], (11.018 g) dissolved in 50 ml of distilled water, together with 0.1 mol of NaOH; the mixture was slowly dropped into the 1,3-dichloropropan-2-ol solution. After ⅔rds of the mixture had been added, the result was a white deposit with a slight pink coloration and the reaction solution increased in temperature. A further 50 ml of methanol was added and heating was effected overnight under reflux (70° C.). The progress of the reaction was tracked by way of DC, with $CH_2Cl_2$ being used as the running agent and thiophenol as the comparison. On the next day the reaction solution was clear, slightly greyish and mixed with oily beads. The reaction time was about 20 hours at 70° C.

The solution was firstly concentrated on the rotational evaporator and then shaken out with $CH_2Cl_2$ (three times with about 100 ml) and dried over $Na_2SO_4$. Concentration was then effected firstly on the rotational evaporator and then on the hybrid oil pump (p=1.8-1.6 mbars, T=30° C.).

Characterisation:

1,3-Bisphenylsulphanyl-propan-2-ol: 13.63 g of a yellowish oily liquid (0.0481 mol); yield 98.6% of theory with respect to 0.05 mol of 1,3-dichloropropan-2-ol;

$^1$H-NMR: 7.32-7.35 ppm (4H, m, H3), 7.24-7.29 ppm (4H, m, H2), 7.17-7.21 ppm (2H, m, H1), 3.78-3.82 ppm (1H, m, $^2$J (5,6)=3.7 Hz, H6), 3.18-3.22 ppm (2H, dd, $^2$J (4,4')=13.9 Hz, $^2$J (4,5)=4.9 Hz, H5), 3.01-3.05 ppm (2H, dd, $^2$J (4',4)=13.7 Hz, $^2$J (4',5)=7.3 Hz, H5'), 2.71 ppm (1H, d, $^2$J (6,5)=3.4 Hz, —OH)

$^{13}$C-NMR: 125.69 MHz in $CD_3OD$ 137.51 ppm (C4), 130.50 ppm (C3), 130.02 ppm (C2), 127.17 ppm (C1), 70.08 ppm (C6), 40.45 ppm (C5).

EXAMPLE 5

Synthesis of

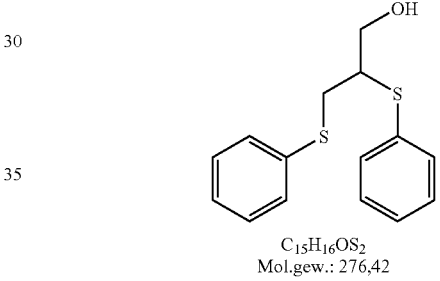

(In the Above Mol.Gew. Means Molecular Weight)
Reaction Equation

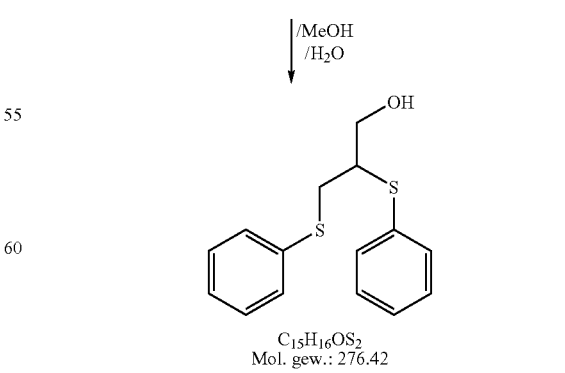

(In the Above Mol.Gew. Means Molecular Weight)

Reagents

Thiophenol (as in Example 4)

2,3-Dichloropropan-1-ol [97.0% (GC)]

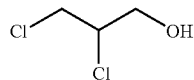

Sodium hydroxide, pellets 99.998%

Experimental Part

Using a 500 ml three-necked flask equipped with a condenser, a dropping funnel and $N_2$ introduction, 0.05 mol of 2,3-dichloropropan-1-ol [97% (GC) (6.449 g)] dissolved in 100 ml of methanol was introduced in an $N_2$ atmosphere. 0.1 mol of thiophenol [$^{98}$%] (11.018 g) dissolved in 50 ml of distilled water and 0.1 mol of NaOH (4.0 g) dissolved in 50 ml of distilled water were added to a dropping funnel. That solution was slowly dropped into the 1,3-dichloropropan-2-ol solution. The result was a slightly pink coloration and the reaction solution increased in temperature. The progress of the reaction was tracked by way of DC, wherein $CH_2Cl_2$ was used as the running agent and thiophenol as the comparison. A further 50 ml of methanol was added and heating was effected overnight under reflux (70° C.). On the next day the reaction solution was clear, slightly greyish and mixed with oily beads. The reaction time was about 20 hours at 70° C.

The solution was firstly concentrated on the rotational evaporator and then shaken out with $CH_2Cl_2$ (three times with about 100 ml) and dried over $Na_2SO_4$. Concentration was then effected firstly on a rotational evaporator and then on the hybrid oil pump.

The result obtained was 12.85 g (0.0465 mol) of a yellowish oily liquid. That corresponded to a yield of 93% of theory with respect to 0.5 mol of 2,3-dichloropropan-1-ol.

Characterisation:

The product was investigated with $^1$H-NMR+$^{13}$C-NMR in $CD_3$-OD. There was an isomer mixture with ca. 80% of the compound with 20% of the propan-2-ol derivative.

The refractive index was determined at: $\eta$=1.6255/T=25.3° C.

EXAMPLE 6

Synthesis of

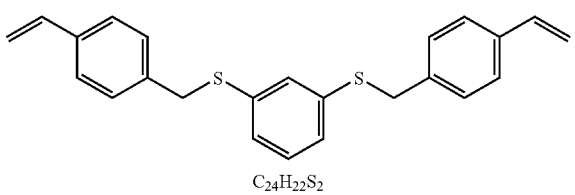

$C_{24}H_{22}S_2$
Mol.gew.:374,56

(In the Above Mol.Gew. Means Molecular Weight)

Reaction Equation

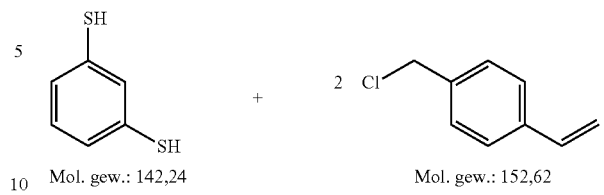

Mol. gew.: 142,24    Mol. gew.: 152,62

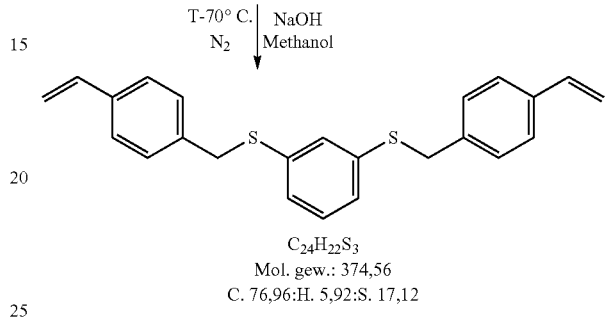

$C_{24}H_{22}S_3$
Mol. gew.: 374,56
C. 76,96:H. 5,92:S. 17,12

(In the Above Mol.Gew. Means Molecular Weight)

Reagents

Benzene-1,3-dithiol, 99%

4-Vinylbenzyl chloride, technically 90% (GC)

Experimental Part

Using a 250 ml three-necked flask equipped with a condenser, a dropping funnel and $N_2$ introduction, 0.01 mol of 1,3-dithiobenzene [99%] (1.437 g) and 0.02 mol of NaOH (about 0.8 g) dissolved in about 30 ml of water were introduced into the flask.

The result was a colourless crystalline deposit. The mixture was heated to 40° C. and 80 ml of methanol was added. The result was a milky solution. Then 0.02 mol of 4-vinylbenzyl chloride [≥90%] (3.0524 g) was added, an emulsion being formed. In order to dissolve the remaining proportion of the 4-vinylbenzyl chloride, a further 60 ml of methanol was added. The mixture was heated to 70° C. and then kept under reflux overnight (about 65° C.). After 23 hours of reaction time the reaction solution was filtered off and extracted with ether (three times with 80 ml on each occasion). The combined ether phases were then shaken out firstly with 80 ml of 1n NaOH and then with distilled water and then dried over sodium sulphate and concentrated on a rotational evaporator (35° C., p=700-750 mbars).

1.82 g of a yellowish oily liquid was obtained. Methanol was added and heating to 66° C. was effected. In that case almost everything was dissolved and the yellow colour disappeared. Hot filtration was then effected and the filter slightly heated. In that case colourless needles immediately precipitated. Suction removal was effected over a G3 frit and drying was then effected on a hybrid oil pump (first p=120 mbars, then 0.12 mbar). The yield was 0.76 g (0.00203 mol), which corresponded to 20.3% of theory.

$^1$H-NMR: 499.84 MHz in $CD_2Cl_2$ 7.33 ppm (4H, d, $^2$J (4,5)=8.1 Hz, H4), 7.22 ppm (4H, d, $^2$J (5,4)=8.1 Hz, H5), 7.185-7.20 ppm (1H, m, H11), 7.01-7.16 ppm (3H, m, 2H9, 1H10), 6.68 ppm (2H, q, $^2$J (2,1')=11.0 Hz, $^2$J (2,1)=17.6 Hz, H2), 5.73 ppm (2H, dd, $^2$J (1,1')=1.0 Hz, $^2$J (1,2)=17.6 Hz, H1), 5.22 ppm (2H, dd, $^2$J (1',2)=11.0 Hz, $^2$J (1',1)=1.0 Hz, H1'), 4.05 ppm (4H, s, H7), $^{13}$C-NMR: 125.69 MHz in CD$_2$Cl$_2$ C3 137.42 ppm, C6 137.25 ppm, C8 136.87 ppm, C2 136.58 ppm, C11 130.23 ppm, C10 129.33 ppm, C5 129.26 ppm, C9 127.59 ppm, C4 126.53 ppm, C1 113.93 ppm, C7 38.56 ppm.

EXAMPLE 7

1.0 g of the monomer of Example 1 was mixed with 0.2% of Irgarcure 2022 and filled between two silanised object carriers which were separated by a spacer of a thickness of 0.9 mm. Photopolymerisation was effected for 2 hours in an N$_2$ atmosphere with a UV lamp of the brand 'Super Actinic' (Lampe TL-D15W/03, $\lambda_{max}$=420 nm, radiation distance 18 cm). Crosslinking of the polymer was achieved by the addition of 3% of ethylene glycol dimethacrylate.

The invention claimed is:

1. An intraocular lens capable of being folded or rolled for implantation into an eye, the intraocular lens comprising a polymer composition, wherein the polymer composition is prepared by polymerisation of:

a) at least one main monomer (a) having the following formula:

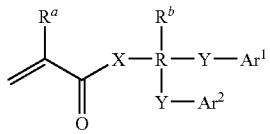

wherein:

X is O or NR$^c$;

Y is O, S or NR$^c$;

R is a straight, branched or cyclic hydrocarbon residue with 1 to 6 carbon atoms;

R$^a$ is hydrogen or a methyl residue;

R$^b$ is hydrogen, a C$_1$-C$_5$ alkyl residue or Y—Ar$^3$;

R$^c$ is hydrogen, a straight, branched or cyclic hydrocarbon residue with 1 to 6 carbon atoms or an aryl group;

Ar$^1$, Ar$^2$ and Ar$^3$ are each independently an aryl group which is bonded to Y by way of a direct bond or by way of a (—CH$_2$—)$_n$ linkage, wherein n is 0, 1, 2 or 3; and b) a crosslinking monomer (b).

2. The intraocular lens of claim 1, wherein Y is S.

3. The intraocular lens of claim 1, wherein the main monomer is selected from one of the following:

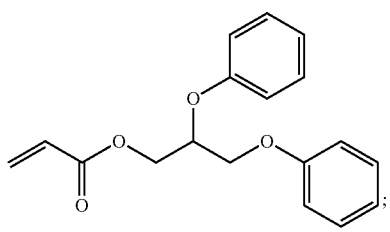

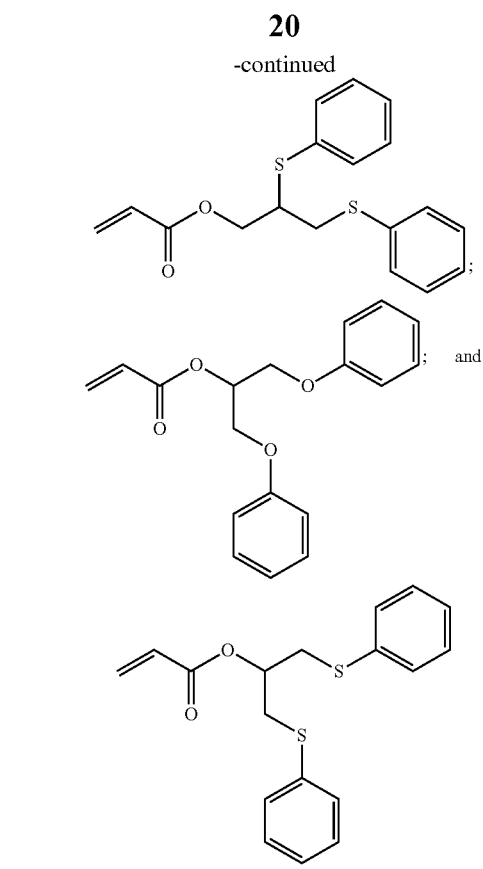

or a mixture thereof.

4. The intraocular lens of claim 1, wherein phenyloxyethyl methacrylate (POEMA) or hydroxyethyl methacrylate (HEMA) is used as monomer (c).

5. The intraocular lens of claim 1, wherein a compound of the following formula II is used as the crosslinking monomer (b):

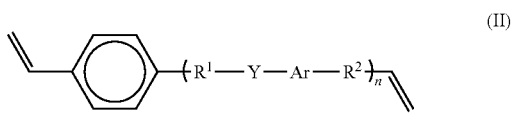

wherein:

Y is O or S;

Ar is an aromatic optionally substituted with 1 to 4 substituents selected from C$_1$-C$_5$ alkyl residues, C$_1$-C$_5$ alkoxy residues and halogens;

n is an integer of 1 to 4; and

R$^1$ and R$^2$ are each independently a bond or a (—CH$_2$—)$_m$ residue wherein m is 1, 2 or 3.

6. The intraocular lens of claim 1, wherein one of the following compounds is used as the crosslinking monomer:

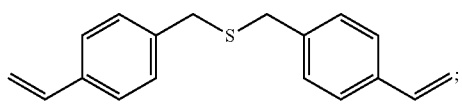

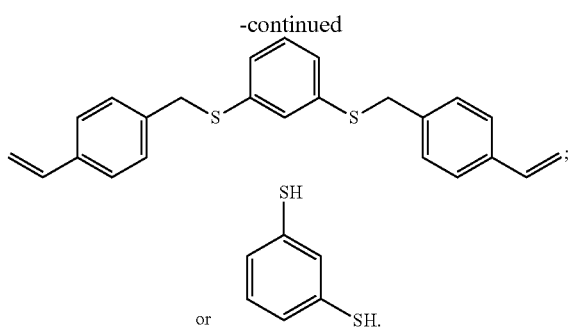

7. The intraocular lens of claim 1, wherein main monomer (a) is present in a proportion of at least 30% by weight.

8. The intraocular lens of claim 1, wherein the polymer composition has a refractive index of 1.60 or more.

9. A method, comprising:
preparing a polymer composition for use in an intraocular lens and capable of being folded or rolled for implantation into an eye, wherein the polymer composition is prepared by polymerisation of:
at least one main monomer (a) having the following formula:

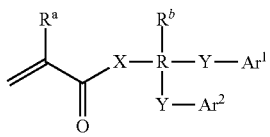

wherein:
X is O or $NR^c$;
Y is O, S or $NR^c$;
R is a straight, branched or cyclic hydrocarbon residue with 1 to 6 carbon atoms;
$R^a$ is hydrogen or a methyl residue;
$R^b$ is hydrogen, a $C_1$-$C_5$ alkyl residue or Y—$Ar^3$;
$R^c$ is hydrogen, a straight, branched or cyclic hydrocarbon residue with 1 to 6 carbon atoms or an aryl group;
$Ar^1$, $Ar^2$ and $Ar^3$ are each independently an aryl group which is bonded to Y by way of a direct bond or by way of (—$CH_2$—)$_n$ linkage, wherein n is 0, 1, 2 or 3; and
a crosslinking monomer (b); wherein the preparing includes:
preparing a prepolymer from main monomer (a) in the presence of a first initiator; and
further polymerizing the prepolymer in the presence of the crosslinking monomer (b), and a second initiator; and
shaping the polymer composition into the intraocular lens.

10. The process according to claim 9, wherein the first and second initiators are the same.

11. The process according to claim 9, wherein the first and second initiators are activatable by light.

12. The intraocular lens of claim 5, wherein Ar is phenyl.

13. The intraocular lens of claim 5, wherein n is 1 or 2.

14. An intraocular lens capable of being folded or rolled for implantation into an eye, the intraocular lens comprising a polymer composition, wherein the polymer composition is prepared by polymerisation of:

a) at least one main monomer selected from one of the following:

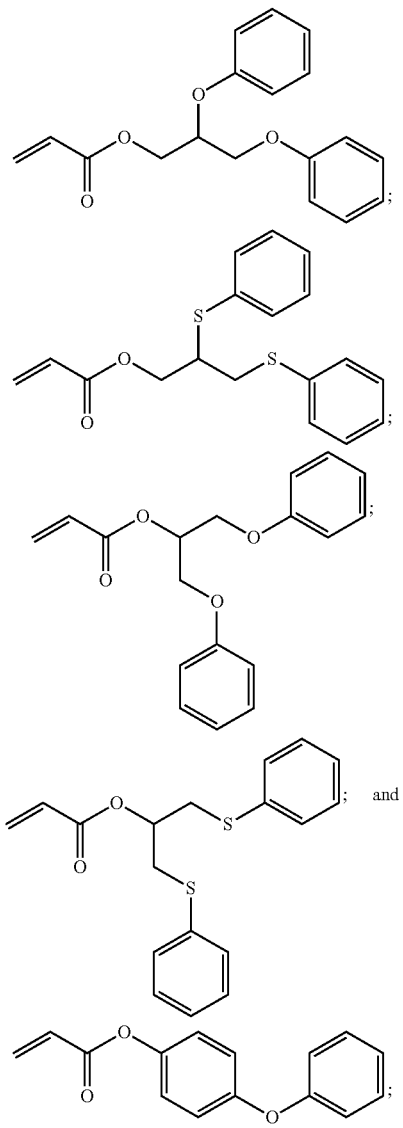

or a mixture thereof;
b) a crosslinking monomer.

15. The intraocular lens of claim 14, wherein the polymer composition is prepared by polymerisation of the at least one main monomer, the crosslinking monomer, and monomers capable of adjusting the refractive index, surface properties, glass transition temperature, strength properties, UV absorption and/or colouring of the polymer composition.

16. The intraocular lens of claim 1, wherein the polymer composition is prepared by polymerisation of the at least one main monomer, the crosslinking monomer, and further monomers capable of adjusting the refractive index, surface properties, glass transition temperature, strength properties, UV absorption and/or colouring of the polymer composition.

17. The method according to claim 9, wherein the aryl group is substituted with 1 to 4 substituents selected from $C_1$-$C_5$ alkyl, $C_1$-$C_5$-alkoxy, mono- and disubstituted amino and $R^c$.

18. The method according to claim 9, wherein:
preparing the polymer composition includes preparing the polymer composition with further monomers (c) capable of adjusting the refractive index, surface properties, glass transition temperature, strength properties, UV absorption and/or colouring of the polymer composition.

19. The method according to claim 18, wherein preparing the prepolymer includes preparing the prepolymer from main monomer (a) and the further monomers in the presence of the first initiator.

20. The method according to claim 19, wherein further polymerizing the prepolymer includes further polymerizing the prepolymer in the presence of the crosslinking monomer (b), further monomers (a), further monomers (c) and the second initiator.

* * * * *